United States Patent [19]
Hosaka et al.

[11] Patent Number: 5,603,329
[45] Date of Patent: Feb. 18, 1997

[54] MULTI-FUNCTIONAL BLOOD PRESSURE MONITOR

[75] Inventors: Hidehiro Hosaka; Takashi Nakaya; Yoshihiro Sugo; Hiromitsu Kasuya; Rie Tanaka, all of Tokyo, Japan

[73] Assignee: Nihon Kohden Corporation, Tokyo, Japan

[21] Appl. No.: 492,938

[22] Filed: Jun. 21, 1995

[30] Foreign Application Priority Data

Jun. 21, 1994 [JP] Japan .................................. 6-138460

[51] Int. Cl.$^6$ .................................................. A61B 05/00
[52] U.S. Cl. .......................... 128/680; 128/681; 128/687; 128/682
[58] Field of Search .................... 128/672, 677, 128/680–3, 687, 690

[56] References Cited

U.S. PATENT DOCUMENTS

| | | | |
|---|---|---|---|
| 4,907,956 | 3/1990 | Schmid et al. | 128/672 |
| 5,237,997 | 8/1993 | Gruebel et al. | 128/672 |

OTHER PUBLICATIONS

"On the Pressure–Volume Relationship in Circulatory Elements", Medical and Biological Engineering & Computing, Hardy et al., Sep. 1982, pp. 565–570.

"The Velocity of the Pulse Wave in Man", J. C. Bramwell et al., Feb. 4, 1992, pp. 298–306.

Primary Examiner—Robert L. Nasser
Attorney, Agent, or Firm—Sughrue, Mion, Zinn, Macpeak & Seas

[57] ABSTRACT

The multi-functional blood pressure monitor includes input unit for entering a value of blood pressure for calibration; unit for detecting a time interval detection reference point on an aortic pulse wave, unit for detecting a peripheral blood pulse wave as it appears later than the aortic pulse wave, unit (CPU) for measuring the pulse wave propagation time on the basis of the detection outputs from the unit for detecting a time interval detection reference point and the unit for detecting a peripheral blood pulse wave, first computing unit (CPU) for computing the values of parameters $\alpha$ and $\beta$ using the two values of blood pressure that have been entered for calibration and the two pulse wave propagation times that have been measured for calibration, second computing unit (CPU) for computing blood pressure from a measured pulse wave propagation time and the values of parameters $\alpha$ and $\beta$, and display for presenting both the computed blood pressure and the value of parameter $\alpha$ which serves as an index for arteriosclerosis.

2 Claims, 3 Drawing Sheets

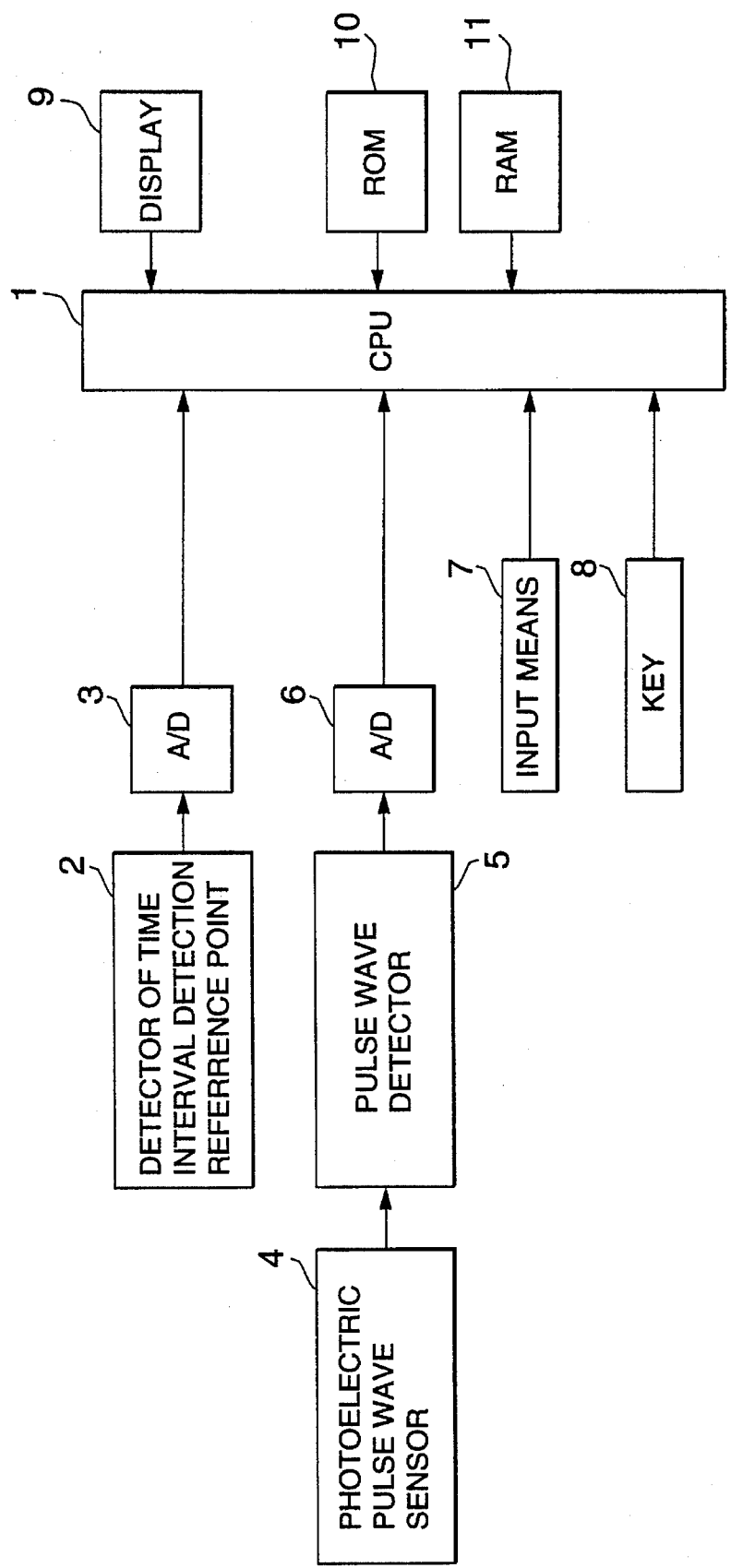

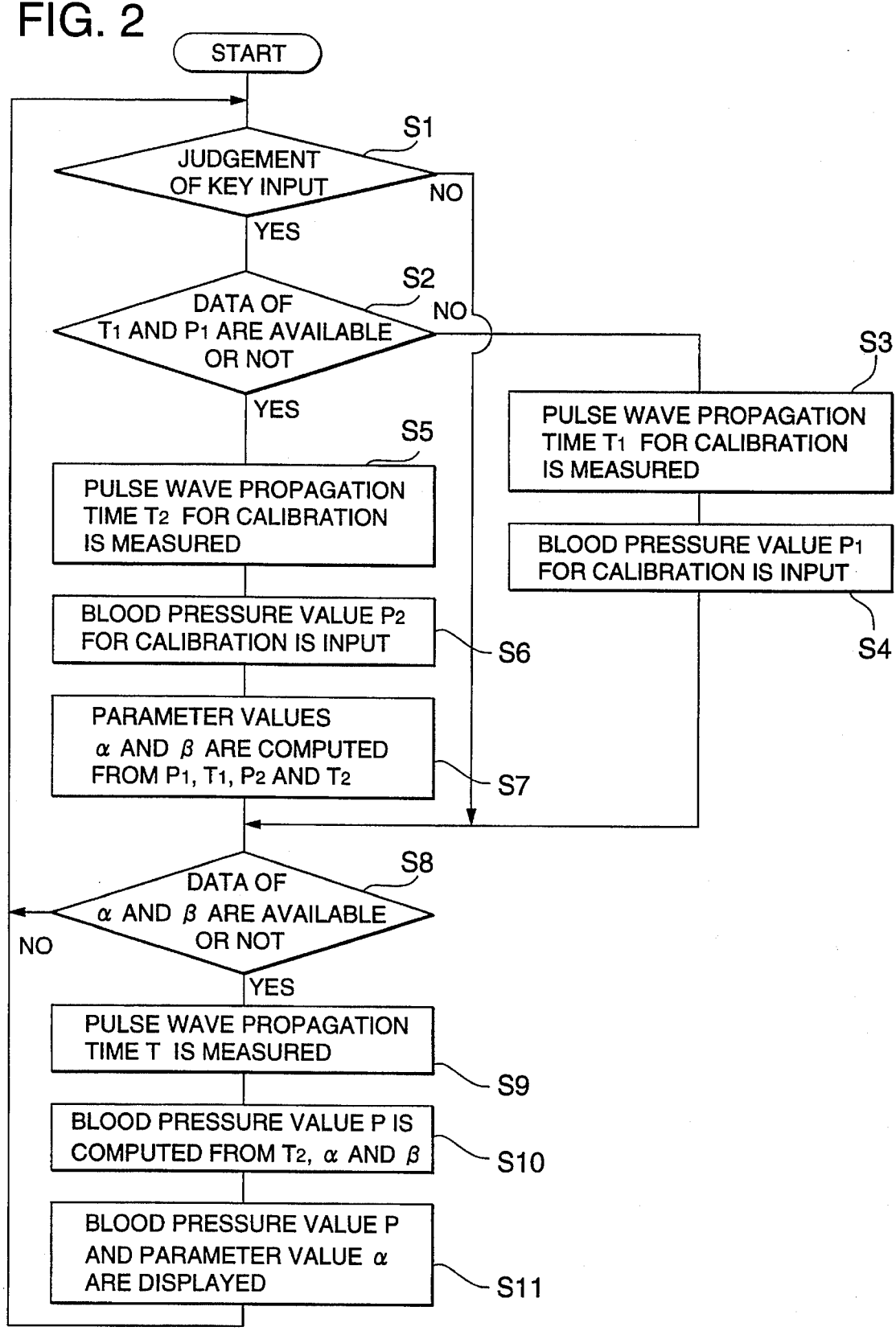

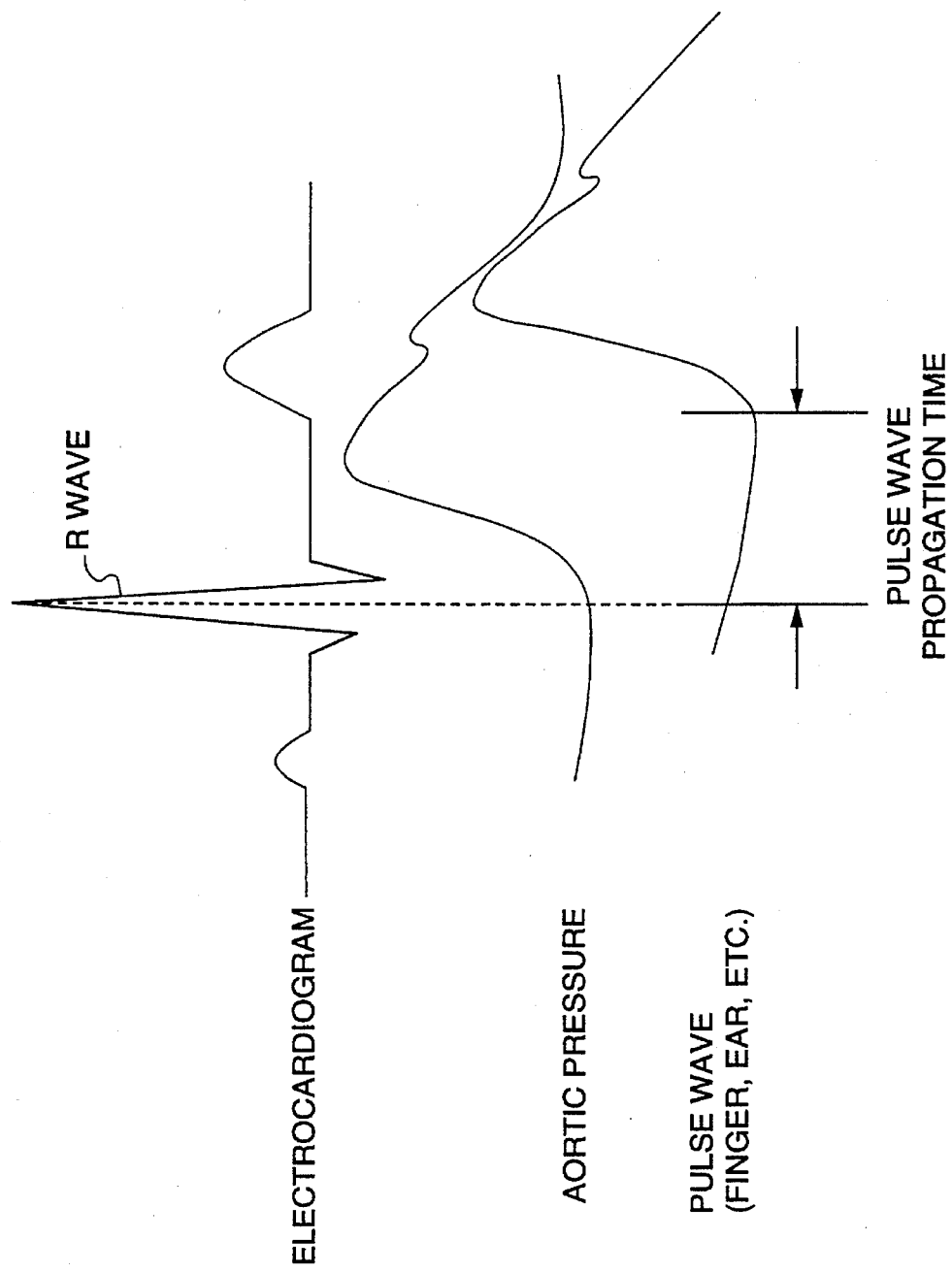

MULTI-FUNCTIONAL BLOOD PRESSURE MONITOR

BACKGROUND OF THE INVENTION

The present invention relates to a multi-functional blood pressure monitor which can measure blood pressure simultaneously with the indication of the degree of arteriosclerosis. More specifically, the invention relates to a blood pressure monitor that measures blood pressure using the pulse wave propagation time.

Cerebral apoplexy and heart attack are two fatal diseases in circulatory organs; cerebral hemorrhage and infarction are causes of the apoplexy, and angina pectoris and myocardial infarction are causes of the heart attack. The primary causes of such circulatory diseases are hypertension and arteriosclerosis, which are interrelated in such a way that hypertension is a risk factor to arteriosclerosis and vice versa. Hence, blood pressure and arteriosclerosis are both important test items and it is desirable to diagnose them simultaneously.

Conventionally, blood pressure is measured by a noninvasive approach using cuffs, and pulse rate is the only other parameter that can be measured with the existing blood pressure monitors. In contrast, arteriosclerosis measurements are performed by dedicated means such as an ophthalmography camera or an angiographic device.

The prior art practice of using dedicated means in arteriosclerosis measurements has involved several problems. First, the testing time is prolonged; second, the initial investment is high; third, there is no convenient way to measure arteriosclerosis at home.

SUMMARY OF THE INVENTION

The present invention has been accomplished under these circumstances and has as an object providing a multi-functional blood pressure monitor that is capable of measuring blood pressure simultaneously with the indication of the degree of arteriosclerosis in a simple manner.

The multi-functional blood pressure monitor of the invention comprises: input means for entering a value of blood pressure for calibration; means for detecting a time interval detection reference point on an aortic pulse wave from a subject; means for detecting a peripheral blood pulse wave as it appears later than said aortic pulse wave; means for measuring the pulse wave propagation time on the basis of the detection outputs from said means for detecting a time interval detection reference point and said means for detecting a peripheral blood pulse wave; first computing means for computing the values of two parameters $\alpha$ and $\beta$ which are characteristic of the subject, $\alpha$ being the parameter by which the pulse wave propagation time is to be multiplied when computing a value of blood pressure from said pulse wave propagation time, and $\beta$ being the parameter to be added when computing blood pressure from the pulse wave propagation time, using two values of blood pressure for calibration and two pulse wave propagation times for calibration, each being obtained by supplying different measurement conditions to the same subject; second computing means for computing blood pressure from an actually measured pulse wave propagation time and said two parameters $\alpha$ and $\beta$; and output means for outputting the computed blood pressure and the value of said parameter $\alpha$ which is an index for arteriosclerosis.

The monitor having the above-described construction can output not only blood pressure but also the value of parameter $\alpha$ which serves as an index for arteriosclerosis and, hence, the measurement of blood vessel and the indication of the degree of arteriosclerosis can be accomplished simultaneously in a simple manner.

BRIEF DESCRIPTION OF THE DRAWINGS

FIG. 1 is a block diagram showing a multi-functional blood pressure monitor according to an embodiment of the invention;

FIG. 2 is a flowchart showing the sequence of steps involved in the operation of the multi-functional blood pressure monitor shown in FIG. 1; and FIG. 3 waveforms for illustrating the pulse wave propagation time.

DETAILED DESCRIPTION OF THE INVENTION

The basic concept of the present invention will be first described.

Among blood pressure monitors operating on the noninvasive approach, one that measures blood pressure using the pulse wave propagation velocity (the time required for a pulse wave to travel a given distance) is known. The theory of blood pressure measurement from the pulse wave propagation velocity is as follows.

The pulse wave propagation time is first explained. In peripheral blood vessels as in a finger or an ear, a bottom of a pulse wave appears later than a bottom of an aortic pressure (see FIG. 3). The time of this delay is called the "pulse wave propagation time".

The pulse wave propagation velocity corresponding to the time required for a pulse wave to travel a given distance is expressed as a function of the volumetric elasticity of a blood vessel of interest. As blood pressure rises, the volumetric pressure of the blood vessel increases and this is why the variation in blood pressure can be determined from the pulse wave propagation velocity.

Before using a blood pressure monitor that operates on the pulse wave propagation time, it is necessary that actual blood pressure be measured by another method such as one using a cuff so that the results of this measurement are employed as a reference for calibration purposes. To obtain calibration data, blood pressure and pulse wave propagation time are measured under two different conditions, for example, at rest and under exercise stress.

Let us write the blood pressure and the pulse wave propagation time at rest as P1 and T1, respectively; the respective values under exercise stress as P2 and T2; and two parameters characteristic of the subject as $\alpha$ and $\beta$. Then, the two values of blood pressure P1 and P2 are given by:

$$P1 = \alpha T1 + \beta \qquad (1)$$

$$P2 = \alpha T2 + \beta \qquad (2)$$

Hence, $\alpha$ and $\beta$ can be computed by substituting the measured values of P1, T1, P2 and T2 into eqs. (1) and (2). Once $\alpha$ and $\beta$ are determined, the blood pressure of the subject can be known by merely measuring the pulse wave propagation time. It should be noted that two different values of blood pressure need not necessarily be measured at rest and under exercise stress but on any occasions where two different values of blood pressure will appear.

Parameter $\alpha$ obtained for the calibration reflects the stiffness of the blood vessel of interest and can be used as an index for the degree of arteriosclerosis.

Therefore, if the value of blood pressure as determined from the pulse wave propagation time is indicated simultaneously with the value of parameter $\alpha$, one can access the result of blood pressure measurement simultaneously with the degree of arteriosclerosis.

In the following, the principle of the present invention, that is, the facts that pameter $\alpha$ can be used as an index for the degree of arteriosclerosis, or parameter $\alpha$ relates to the volumetric elasticity of a blood vessel, will be described in more detail.

[1] Relation between volume (V) of a blood vessel and blood pressure (P)

According to the article "On the pressure-volume relationship in circulatory elements" by H. H. Hardy et al., Med. & Biol. Eng. & Comput., 1982, 20, 565–570, as general properties of a blood vessel, since dV/dP (expansion property) tends to zero as P increases, $$dV/dP = \kappa(V_m - V) \quad (i)$$

$\kappa$: constant determined by elastic property of blood vessel wall and surrounding tissue $V_m$: maximum volume of blood vessel From equation (i), $$V = V_m(1 - \kappa_0 \cdot \exp(-\kappa P)) \quad (ii)$$

Where, $\kappa_0$ represents a ratio between a maximum volume of a blood vessel and a volume of the blood vessel changed with the change of the blood pressure (the range of the change is from P=0 to that at which the blood vessel reaches the maximum volume).

[2] Relation between pulse wave propagation time (T) and blood pressure (P)

The volumetric elasticity (K) is expressed by the following general equation (iii).

$$K = V \cdot (dP/dV) \quad (iii)$$

When equation (ii) is substituted for equation (iii), the following equation is obtained.

$$K = \{1 - \kappa_0 \cdot \exp(-\kappa P)\}/\{\kappa_0 \cdot \kappa \cdot \exp(-\kappa P)\} \quad (iv)$$
$$= \exp(\kappa P)/(\kappa_0 \cdot \kappa) - 1/\kappa$$

At the value of $\kappa$ and $\kappa_0$ given by H. H. Hardy et al and within the range of physiological blood pressure P, equation (iv) is approximated as follows.

$$K = \exp(\kappa P)/(\kappa_0 \cdot \kappa) \quad (v)$$

According to the article "The Velocity of the Pulse Wave in Man" by J. C. Bramwell et al, Proc. Roy. Soc. Lond. s.B. Biological Sciences 93: 298–306.1922, the pulse wave propagation velocity (C) relates to volumetric elasticity as follows.

$$C = \sqrt{(K/\rho)} \quad (vi)$$

$\rho$: density of blood

The pulse wave propagation time (T) is expressed by equation (vii) using length (L) of a blood vessel:

$$T = L/C = L \cdot \sqrt{(\rho/K)} \quad (vii)$$

When equation (v) is substituted for equation (vii), $$T = \sqrt{\rho/1/\{\kappa_0 \cdot \kappa \cdot \exp(-\kappa P)\}} \cdot L \quad (viii)$$

[3] Relation between volumetric elasticity K of a blood vessel and parameter $\alpha$ $$1/\alpha = dT/dP = (dT/dK) \cdot (dK/dP) \quad (ix)$$

From equation (viii), $$dT/dK = -L/2 \cdot \sqrt{\rho} \cdot \{\kappa_0 \cdot \kappa \cdot \exp(-\kappa P)\}^{3/2} \quad (x)$$

From equation (v), $$dK/dP = \exp(\kappa P)/\kappa_0 \quad (xi)$$

By substituting equations (x) and (xi) for equation (ix), parameter $\alpha$ is obtained as follows.

$$\alpha = -(2/L) \cdot (1/\sqrt{\rho}) \cdot (1/\sqrt{\kappa_0}) \cdot \kappa^{-3/2} \cdot \exp(\kappa P)^{1/2} \quad (xii)$$

At the value of $\kappa$ by H. H. Hardy et al and within the range of physiological blood pressure P, $\exp(\kappa P)^{1/2}$ is dominant in parameter $\alpha$.

As is apparent from equation (v), the volumetric elasticity K of a blood vessel relates to constant $\kappa$. Further, from equation (12), $|\alpha|$ also relates to constant $\kappa$. Accordingly, the blood vessel elasticity K relates to parameter $\alpha$.

Next, a preferred embodiment of the invention will be described in detail with reference to FIGS. 1 and 2.

FIG. 1 is a block diagram showing a multi-functional blood pressure monitor according to an embodiment of the invention. Indicated by 2 is a detector of a time interval detection reference point, which serves to detect the point of time when the aortic pressure reaches a bottom almost simultaneously with the generation of the R wave on an electrocardiogram (ECG). The output of the detector 2 is supplied to an A/D converter 3 for conversion to a digital signal, which is then supplied to a CPU (central processing unit) 1. The detector 2 may be composed of an electrode to be placed on the chest of a subject and an ECG R-wave detector to which the electrode is connected. Alternatively, the detector 2 may be composed of a photoelectric pulse wave sensor or a pressure sensor that can detect pulse waves from the aorta and a pulse wave detector to which the sensor is connected.

Shown by 4 is a photoelectric pulse wave sensor which may be attached to, for example, a finger of the subject for measuring pulse waves from peripheral blood vessels. The output of the sensor 4 is fed to a pulse wave detector 5 for detecting the pulse wave as it originates from the site at which the sensor 4 is attached. The output of the pulse wave detector 5 is fed into an A/D converter 6 for conversion to a digital signal, which is also supplied to the CPU 1.

Shown by 8 is a key pad which is touched in the calibration process to determine the values of parameters and $\beta$ and $\beta$ characteristic of the subject.

Shown by 7 is input means from which two values of blood pressure for calibration, P1 and P2, are entered.

The CPU 1 executes a predetermined processing program on the basis of signals supplied from the A/D converters 3 and 6, the keypad 8 and the input means 7, and the result of the processing is indicated on a display 9 as output means.

The CPU 1 is connected to two memories, one being ROM 10 for storing the processing program and the other being RAM 11 for storing the data being processed. The CPU 1 corresponds to means for measuring the pulse wave propagation time, first computing means and second computing means in claims.

The multi-functional blood pressure monitor having the construction described above will operate in the sequence of steps outlined in the FIG. 2 flowchart.

The operation starts with step S1, in which question is asked if input data have been entered from the keypad 8. If the answer is affirmative, the process goes to step S2 and question is asked if T1 (pulse wave propagation time) and P1 (blood pressure) are available as data. If the answer is negative, the process goes to step S3, in which data entered from the A/D converters 3 and 6 are processed with the CPU 1 and T1 for calibration is measured. The measured value of T1 is written into the RAM 11.

In subsequent step S4, a separate blood pressure monitor with a cuff is used to measure P1, or the value of blood pressure developing just after the measurement of T1, and the result is entered as P1 for calibration from the input means 7. The entered P1 is written into the RAM 11, whereupon the measurements of T1 and P1 end.

Subsequently, an exercise stress is applied to the subject in step S2 and input data are entered from the keypad 8. If T1 and P1 are available as data, the process goes to step S5, in which data entered from the A/D converters 3 and 6 are processed with the CPU 1 and T2 for calibration is measured. The measured value of T2 is written into the RAM 11.

In subsequent step S6, P2, or the value of blood pressure developing just after the measurement of T2, is measured and the result is entered as P2 for calibration from the input means 7. The entered P2 is written into the RAM 11.

The process goes to step 7, in which the values of P1, T1, P2 and T2 that have been read from the RAM 11 are processed with the CPU 1 to compute the value of parameter $\alpha$ by the following eq. (3) which is derived from eqs. (1) and (2). Additionally, the CPU 1 determines the value of parameter $\beta$ by the following eq. (4). The values of the two parameters are written into the RAM 11:

$$\alpha = (P1 - P2)/(T1 - T2) \quad (3)$$

$$\beta = P1 - \alpha T1 \quad (4)$$

In subsequent step S8, question is asked if the values of parameters $\alpha$ and $\beta$ are available as data. If the answer is affirmative, the process goes to step S9, in which data entered from the A/D converters 3 and 6 are processed with the CPU 1 and the pulse wave propagation time T is measured. The measured value of T is written into the RAM 11.

In subsequent step S10, the values of T, $\alpha$ and $\beta$ being read from the RAM 11 are processed with the CPU 1 to compute the blood pressure P from the following equation, which is then written into the RAM 11:

$$P = \alpha T + \beta$$

In subsequent step S11, the blood pressure P and the value of parameter $\alpha$ which serves as an index for arteriosclerosis are presented on the display 9 as they are read from the RAM 11.

If similar measurements are to be repeated for the same subject, the sequence of steps from S8 through S11 need only to be performed.

As described above, the present invention uses a simple device and yet the measurement of blood pressure and the indication of parameter which is associated with arteriosclerosis can be accomplished simultaneously. In the absence of the need to employ a dedicated apparatus for measuring arteriosclerosis, the problems that have been encountered in the prior art, such as prolonged testing and high investment cost, can be solved. This offers an added advantage in that the degree of arteriosclerosis can easily be estimated at home.

What is claimed is:

1. A multi-functional blood pressure monitor, comprising:

input means for entering a value of blood pressure for calibration;

means for detecting a time interval detection reference point on an aortic pulse wave from a subject;

means for detecting a peripheral blood pulse wave as it appears later than said aortic pulse wave;

means for measuring a pulse wave propagation time on the basis of detection outputs from said means for detecting a time interval detection reference point and said means for detecting a peripheral blood pulse wave;

first computing means for computing values of two parameters $\alpha$ and $\beta$ which are characteristic of the subject, $\alpha$ being a parameter by which the pulse wave propagation time is to be multiplied when computing blood pressure from said pulse wave propagation time, and $\beta$ being a parameter to be added when computing blood pressure from the pulse wave propagation time, using two values of blood pressure for calibration and two pulse wave propagation times for calibration, each being obtained by subjecting the same subject to different measurement conditions;

second computing means for computing blood pressure from an actually measured pulse wave propagation time and said two parameters $\alpha$ and $\beta$; and output means for outputting the computed blood pressure and the value of said parameter $\alpha$ which is an index for arteriosclerosis.

2. A multi-functional blood pressure monitor as claimed in claim 1, wherein said first computing means computes the values of two parameters $\alpha$ and $\beta$ in accordance with the following equations:

$$\alpha = (P1 - P2)/(T1 - T2)$$

$$\beta = P1 - \alpha T1$$

where P1 is a first blood pressure value, P2 is a second blood pressure value different from the first blood pressure value, T1 is a pulse wave propagation time at the blood pressure value P1, and T2 is a pulse wave propagation time at the blood pressure value P2.

* * * * *